United States Patent [19]
Klee et al.

[11] Patent Number: 5,876,210
[45] Date of Patent: *Mar. 2, 1999

[54] DENTAL POLYMER PRODUCT

[75] Inventors: Joachim E. Klee, Radolfzell; Walter Leube, Freiburg, both of Germany

[73] Assignee: Dentsply G.m.b.H., Germany

[ * ] Notice: This patent issued on a continued prosecution application filed under 37 CFR 1.53(d), and is subject to the twenty year patent term provisions of 35 U.S.C. 154(a)(2).

[21] Appl. No.: 754,664

[22] Filed: Nov. 21, 1996

Related U.S. Application Data

[63] Continuation of Ser. No. 231,535, Apr. 22, 1994, abandoned.

[51] Int. Cl.$^6$ .................... A61C 5/00; C08L 63/00
[52] U.S. Cl. ............... 433/226; 433/228.1; 523/105; 523/137; 523/400; 523/401; 523/442; 523/444; 523/458; 523/459; 523/460; 525/504; 525/510; 525/529; 525/533; 525/903; 525/922
[58] Field of Search ................... 525/504, 510, 525/529, 533, 903, 922; 523/105, 137, 400, 401, 442, 444, 458, 459, 460; 433/226, 228.1

[56] References Cited

U.S. PATENT DOCUMENTS

| | | | |
|---|---|---|---|
| 150,262 | 4/1874 | Slavin | 604/218 |
| 173,850 | 2/1876 | Emde | 604/218 |
| D. 195,391 | 6/1963 | Pakison | D81/1 |
| 212,975 | 4/1879 | Perkins et al. | 604/218 |
| D. 315,956 | 4/1991 | Dragan | D24/14 |
| D. 353,673 | 12/1994 | Discko, Jr. et al. | D24/152 |
| 543,829 | 7/1895 | Gurnee | 604/218 |
| 3,066,112 | 11/1962 | Bowen | 260/1 |
| 3,150,801 | 9/1964 | Hamilton | 222/158 |
| 3,200,142 | 8/1965 | Bowen | 260/286 |
| 3,256,226 | 6/1966 | Fekete | 260/23.5 |
| 3,317,469 | 5/1967 | Feichtinger et al. | 260/47 |
| 3,327,016 | 6/1967 | Lee | 260/830 |
| 3,327,017 | 6/1967 | Huang et al. | 260/844 |
| 3,466,259 | 9/1969 | Jernigan | 260/37 |
| 3,503,128 | 3/1970 | Boyd et al. | 32/15 |
| 3,539,533 | 11/1970 | Lee, II et al. | 260/17 |
| 3,564,074 | 2/1971 | Swisher et al. | 260/837 |
| 3,586,527 | 6/1971 | Aronoff et al. | 117/93.31 |
| 3,595,969 | 7/1971 | Shepherd et al. | 260/28.5 |
| 3,634,542 | 1/1972 | Dowd et al. | 260/837 |
| 3,673,558 | 6/1972 | Toepel et al. | 260/29.2 |
| 3,706,866 | 12/1972 | Waller | 260/27 |
| 3,709,866 | 1/1973 | Waller | 260/27 |
| 3,742,949 | 7/1973 | Hill | 128/218 |
| 3,754,054 | 8/1973 | Khnura et al. | 260/860 |
| 3,769,336 | 10/1973 | Lee, Jr. et al. | 260/486 |
| 3,815,239 | 6/1974 | Lee, Jr. et al. | 32/15 |
| 3,835,090 | 9/1974 | Gander et al. | 260/42.15 |
| 3,845,009 | 10/1974 | Gander | 260/42.15 |
| 3,853,962 | 12/1974 | Gander | 260/486 |
| 3,882,187 | 5/1975 | Takiyama et al. | 260/835 |
| 3,889,385 | 6/1975 | Dougherty | 32/12 |
| 3,926,906 | 12/1975 | Lee, II et al. | 260/42.53 |
| 3,971,765 | 7/1976 | Green et al. | 260/78 |
| 3,973,972 | 8/1976 | Muller | 106/39.7 |
| 3,980,483 | 9/1976 | Nishikubo et al. | 96/115 |
| 4,002,669 | 1/1977 | Gross et al. | 260/486 |
| 4,051,195 | 9/1977 | McWhorter | 525/530 |
| 4,081,492 | 3/1978 | Traenckner et al. | 260/837 |
| 4,097,569 | 6/1978 | Waters | 264/255 |
| 4,097,994 | 7/1978 | Reaville et al. | 32/15 |
| 4,098,735 | 7/1978 | Tobias | 260/18 |
| 4,100,045 | 7/1978 | Bogan et al. | 204/159.16 |

(List continued on next page.)

FOREIGN PATENT DOCUMENTS

| | | |
|---|---|---|
| 563464 | 9/1958 | Canada . |
| 817442 | 7/1969 | Canada . |
| 1107751 | 8/1971 | Canada . |
| 878004 | 8/1971 | Canada . |
| 878006 | 8/1971 | Canada . |
| 966500 | 4/1975 | Canada . |
| 983491 | 2/1976 | Canada . |
| 987044 | 4/1976 | Canada . |
| 995667 | 8/1976 | Canada . |
| 1018294 | 9/1977 | Canada . |
| 1030979 | 5/1978 | Canada . |

(List continued on next page.)

OTHER PUBLICATIONS

Encyclopedia of Science and Technology, vol. 6, pp. 340–354, 1986.

"Encyclopedia of Polymer Science and Engineering", vol. 8, Identification to Lignin, John Wiley and Sons, Oct. 1987.

Lal et al; Journal of Polymer Science: vol. XXIV, pp. 75–84 (1957) New Polymerization Catalysts for Methyl Methacrylate.

Beaunez et al: Journal of Polymer Science: Part A: Polymer Chemistry, vol. 32, pp. 1459–1469 (1994).

Antonucci et al; Journal of Dental Research 58(9), pp. 1887–1899, Sep. 1979; New Initiator Systems for Dental Resins based on Ascorbic Acid.

Chemistry Abstract 115 (1991) 78952z and Chemistry Abstract 115 (1991) 78973g.

(List continued on next page.)

*Primary Examiner*—Randy Gulakowski
*Attorney, Agent, or Firm*—Dale R. Lovercheck; James B. Bieber

[57] ABSTRACT

The invention concerns a process for preparing a polymer composition, that is free-radical/photochemical and thermal curing epoxide-methacrylate and/or isocyanate-methacrylate adhesives in broadest terms, dental/medical adhesives, and dental restoratives. Furthermore the dual curing epoxide-methacrylate and/or isocyanate-methacrylate adhesives can be used in the optical industry, in optoelectronics and microelectronics, for example for the adhesion of complicated optical components in the combination glass/glass, glass/metal. Advantageous is the small shrinkage during polymerization and the good mechanical properties in combination with the possibility of step-wise or one-step polymerization.

20 Claims, No Drawings

U.S. PATENT DOCUMENTS

| | | | |
|---|---|---|---|
| 4,135,868 | 1/1979 | Schainholz | 422/310 |
| 4,141,865 | 2/1979 | Bogan | 260/18 |
| 4,150,012 | 4/1979 | Joos | 260/42.15 |
| 4,177,563 | 12/1979 | Schmitz-Josten et al. | 433/228 |
| 4,182,035 | 1/1980 | Yamauchi et al. | 433/228 |
| 4,182,833 | 1/1980 | Hicks | 528/120 |
| 4,197,390 | 4/1980 | Jackson | 528/115 |
| 4,220,582 | 9/1980 | Orlowski et al. | 260/42.28 |
| 4,229,376 | 10/1980 | Rogier | 260/563 P |
| 4,253,830 | 3/1981 | Kazen et al. | 433/77 |
| 4,255,468 | 3/1981 | Oson | 427/137 |
| 4,256,457 | 3/1981 | Behring | 433/77 |
| 4,284,742 | 8/1981 | Bowerman, Jr. et al. | 525/329 |
| 4,293,074 | 10/1981 | Dunsky | 206/572 |
| 4,296,004 | 10/1981 | Rogier | 260/18 EP |
| 4,308,085 | 12/1981 | Horhold et al. | 156/330 |
| 4,362,889 | 12/1982 | Bowen | 560/221 |
| 4,368,889 | 1/1983 | Reker, Jr. | 273/243 |
| 4,383,826 | 5/1983 | Butler et al. | 433/228 |
| 4,383,879 | 5/1983 | Le Du et al. | 156/307 |
| 4,384,853 | 5/1983 | Welsh | 433/90 |
| 4,391,590 | 7/1983 | Dougherty | 433/90 |
| 4,405,766 | 9/1983 | Bertram et al. | 525/507 |
| 4,406,625 | 9/1983 | Orlowski et al. | 433/228 |
| 4,413,105 | 11/1983 | Koenig | 525/482 |
| 4,431,421 | 2/1984 | Kawahara et al. | 433/228 |
| 4,446,246 | 5/1984 | McGinniss | 502/155 |
| 4,467,079 | 8/1984 | Hechenberger et al. | 526/90 |
| 4,514,342 | 4/1985 | Billington et al. | 260/952 |
| 4,515,634 | 5/1985 | Wu et al. | 106/35 |
| 4,524,161 | 6/1985 | Feuerhahn | 523/414 |
| 4,541,992 | 9/1985 | Jerge et al. | 422/300 |
| 4,547,531 | 10/1985 | Waknine | 523/116 |
| 4,548,689 | 10/1985 | Sakashita et al. | 204/159.23 |
| 4,557,848 | 12/1985 | Sung et al. | 252/51.5 |
| 4,569,662 | 2/1986 | Dragan | 433/89 |
| 4,579,904 | 4/1986 | Orlowski et al. | 524/554 |
| 4,595,734 | 6/1986 | O'Hearn | 525/524 |
| 4,643,303 | 2/1987 | Arp et al. | 206/370 |
| 4,695,610 | 9/1987 | Egli et al. | 525/426 |
| 4,714,571 | 12/1987 | Schornick et al. | 528/103 |
| 4,714,751 | 12/1987 | Schornick et al. | 528/103 |
| 4,758,643 | 7/1988 | Tanaka et al. | 526/279 |
| 4,767,326 | 8/1988 | Bennett et al. | 433/90 |
| 4,774,063 | 9/1988 | Runnells | 422/297 |
| 4,781,921 | 11/1988 | Smith et al. | 424/81 |
| 4,789,620 | 12/1988 | Sasaki et al. | 430/280 |
| 4,806,381 | 2/1989 | Engelbrecht et al. | 427/2 |
| 4,816,495 | 3/1989 | Blackwell et al. | 522/14 |
| 4,816,528 | 3/1989 | Dervan et al. | 525/438 |
| 4,854,475 | 8/1989 | Riihimaki et al. | 220/337 |
| 4,863,993 | 9/1989 | Montgomery | 524/854 |
| 4,866,146 | 9/1989 | Janda et al. | 526/213 |
| 4,872,936 | 10/1989 | Engelbrecht | 156/307.3 |
| 4,874,799 | 10/1989 | Hung et al. | 522/96 |
| 4,883,899 | 11/1989 | Muramoto et al. | 560/14 |
| 4,918,136 | 4/1990 | Kawaguchi et al. | 524/751 |
| 4,931,096 | 6/1990 | Fujisawa et al. | 106/35 |
| 4,936,775 | 6/1990 | Bennett | 433/220 |
| 4,950,697 | 8/1990 | Chang et al. | 523/116 |
| 4,959,199 | 9/1990 | Brewer | 422/300 |
| 4,963,093 | 10/1990 | Dragan | 433/90 |
| 4,964,911 | 10/1990 | Ibsen et al. | 106/35 |
| 4,969,816 | 11/1990 | Drumm | 433/90 |
| 4,985,198 | 1/1991 | Hirasawa et al. | 560/130 |
| 4,985,516 | 1/1991 | Sakashita et al. | 526/196 |
| 4,996,101 | 2/1991 | Landis et al. | 428/272 |
| 5,006,066 | 4/1991 | Rouse | 433/77 |
| 5,052,927 | 10/1991 | Discko, Jr. | 433/90 |
| 5,083,921 | 1/1992 | Dragan | 433/90 |
| 5,100,320 | 3/1992 | Martin et al. | 433/90 |
| 5,106,301 | 4/1992 | Miyahara et al. | 433/214 |
| 5,108,287 | 4/1992 | Yee et al. | 433/77 |
| 5,110,867 | 5/1992 | Schutyser et al. | 525/903 |
| 5,122,057 | 6/1992 | Discko, Jr. | 433/90 |
| 5,129,825 | 7/1992 | Discko, Jr. | 433/90 |
| 5,137,990 | 8/1992 | Corley | 525/530 |
| 5,151,479 | 9/1992 | Mukai et al. | 526/277 |
| 5,165,890 | 11/1992 | Discko, Jr. | 433/90 |
| 5,166,117 | 11/1992 | Imai et al. | 502/169 |
| 5,172,810 | 12/1992 | Brewer | 206/369 |
| 5,173,273 | 12/1992 | Brewer | 422/300 |
| 5,189,077 | 2/1993 | Kerby | 523/116 |
| 5,204,398 | 4/1993 | Cohen et al. | 524/403 |
| 5,210,157 | 5/1993 | Schutyser et al. | 525/530 |
| 5,215,726 | 6/1993 | Kudla et al. | 422/297 |
| 5,217,372 | 6/1993 | Truocchio | 433/215 |
| 5,235,008 | 8/1993 | Hefner, Jr. et al. | 525/529 |
| 5,236,362 | 8/1993 | Cohen et al. | 433/228.1 |
| 5,252,629 | 10/1993 | Imai et al. | 523/118 |
| 5,267,859 | 12/1993 | Discko, Jr. | 433/89 |
| 5,279,800 | 1/1994 | Berr, Jr. | 422/300 |
| 5,284,632 | 2/1994 | Kudla et al. | 422/297 |
| 5,294,413 | 3/1994 | Riihimaki et al. | 422/297 |
| 5,322,440 | 6/1994 | Steele | 433/90 |
| 5,324,273 | 6/1994 | Discko, Jr. | 604/240 |
| 5,340,551 | 8/1994 | Berry, Jr. | 422/300 |
| 5,345,677 | 9/1994 | Risk | 422/297 |
| 5,360,877 | 11/1994 | Hwang et al. | 525/533 |
| 5,384,103 | 1/1995 | Miller | 422/310 |

FOREIGN PATENT DOCUMENTS

| | | |
|---|---|---|
| 1099848 | 4/1981 | Canada . |
| 1100990 | 5/1981 | Canada . |
| 1107293 | 8/1981 | Canada . |
| 1115289 | 12/1981 | Canada . |
| 1131827 | 9/1982 | Canada . |
| 1140939 | 2/1983 | Canada . |
| 1151667 | 8/1983 | Canada . |
| 1153391 | 9/1983 | Canada . |
| 1155141 | 10/1983 | Canada . |
| 1175196 | 9/1984 | Canada . |
| 1183144 | 2/1985 | Canada . |
| 1185982 | 4/1985 | Canada . |
| 1189996 | 6/1985 | Canada . |
| 1200555 | 2/1986 | Canada . |
| 1202749 | 4/1986 | Canada . |
| 1210777 | 9/1986 | Canada . |
| 1219990 | 3/1987 | Canada . |
| 1227202 | 9/1987 | Canada . |
| 1235423 | 4/1988 | Canada . |
| 1242213 | 9/1988 | Canada . |
| 1248126 | 1/1989 | Canada . |
| 1258465 | 8/1989 | Canada . |
| 2002017 | 5/1990 | Canada . |
| 1270846 | 6/1990 | Canada . |
| 2005912 | 6/1990 | Canada . |
| 2006431 | 6/1990 | Canada . |
| 2006432 | 6/1990 | Canada . |
| 2066433 | 6/1990 | Canada . |
| 2066434 | 6/1990 | Canada . |
| 2004624 | 7/1990 | Canada . |
| 2026009 | 7/1990 | Canada . |
| 1272735 | 8/1990 | Canada . |
| 2009471 | 8/1990 | Canada . |
| 2088895 | 8/1990 | Canada . |
| 2012824 | 9/1990 | Canada . |
| 2014027 | 10/1990 | Canada . |
| 2014359 | 10/1990 | Canada . |
| 1276168 | 11/1990 | Canada . |
| 1276648 | 11/1990 | Canada . |
| 1277070 | 11/1990 | Canada . |
| 2054747 | 11/1990 | Canada . |
| 2010210 | 12/1990 | Canada . |

| | | |
|---|---|---|
| 2018728 | 12/1990 | Canada . |
| 2019210 | 12/1990 | Canada . |
| 2019410 | 12/1990 | Canada . |
| 2054710 | 12/1990 | Canada . |
| 2054757 | 12/1990 | Canada . |
| 1281734 | 3/1991 | Canada . |
| 2026467 | 3/1991 | Canada . |
| 1283121 | 4/1991 | Canada . |
| 1283663 | 4/1991 | Canada . |
| 2027887 | 4/1991 | Canada . |
| 2042587 | 4/1991 | Canada . |
| 2028728 | 5/1991 | Canada . |
| 2032556 | 6/1991 | Canada . |
| 2033405 | 7/1991 | Canada . |
| 2035650 | 8/1991 | Canada . |
| 2026417 | 9/1991 | Canada . |
| 2038332 | 9/1991 | Canada . |
| 1290766 | 10/1991 | Canada . |
| 2045762 | 12/1991 | Canada . |
| 2046373 | 1/1992 | Canada . |
| 1296015 | 2/1992 | Canada . |
| 2049725 | 3/1992 | Canada . |
| 2061230 | 8/1992 | Canada . |
| 2061539 | 8/1992 | Canada . |
| 2041828 | 11/1992 | Canada . |
| 227 363 | 1/1984 | Czechoslovakia . |
| 0 014 515 | 8/1980 | European Pat. Off. . |
| 037 759 | 10/1981 | European Pat. Off. . |
| 120 559 | 1/1983 | European Pat. Off. . |
| 104 491 | 4/1984 | European Pat. Off. . |
| 115 410 | 4/1984 | European Pat. Off. . |
| A-0 104 491 | 4/1984 | European Pat. Off. . |
| 115 948 | 8/1984 | European Pat. Off. . |
| 188 752 | 12/1984 | European Pat. Off. . |
| A-0 188 752 | 7/1986 | European Pat. Off. . |
| 212 193 | 3/1987 | European Pat. Off. . |
| 219 058 | 4/1987 | European Pat. Off. . |
| 277 413 | 10/1988 | European Pat. Off. . |
| 356 868 | 3/1990 | European Pat. Off. . |
| 4141174A1 | 3/1991 | European Pat. Off. . |
| 1 003 448 | 8/1958 | Germany . |
| 2 126 419 | 12/1971 | Germany . |
| 2126419 | 1/1973 | Germany . |
| 141 667 | 5/1980 | Germany . |
| 154 945 | 6/1982 | Germany . |
| 209 358 | 4/1984 | Germany . |
| 208 365 | 5/1984 | Germany . |
| 214 381 | 10/1984 | Germany . |
| 229 140 | 10/1985 | Germany . |
| 229 140 A1 | 10/1985 | Germany . |
| 244 748 | 4/1987 | Germany . |
| 35 36 076 | 4/1987 | Germany . |
| 35 36 077 | 4/1987 | Germany . |
| 248 598 | 8/1987 | Germany . |
| 248 598 A1 | 8/1987 | Germany . |
| 261 365 | 10/1988 | Germany . |
| 4217761.8 | 4/1989 | Germany . |
| 277 078 | 3/1990 | Germany . |
| 277 689 | 4/1990 | Germany . |
| 277 689 A1 | 4/1990 | Germany . |
| A-227 689 | 4/1990 | Germany . |
| 279 667 A1 | 6/1990 | Germany . |
| 279 667 | 8/1990 | Germany . |
| 295758 | 11/1991 | Germany . |
| 41 41 174 | 6/1992 | Germany . |
| 41 09 048 | 9/1992 | Germany . |
| 42 17 761 | 2/1993 | Germany . |
| 3-27308 | 6/1989 | Japan . |
| 1-254727 | 9/1989 | Japan . |
| 1-143846 | 10/1989 | Japan . |
| 4-120540 | 2/1992 | Japan . |
| 4-4219 | 12/1992 | Japan . |
| 52106 | 2/1937 | U.S.S.R. . |
| 311 637 | 8/1971 | U.S.S.R. . |
| 311 638 | 8/1971 | U.S.S.R. . |
| 349 396 | 9/1972 | U.S.S.R. . |
| 545 353 | 2/1977 | U.S.S.R. . |
| 549 150 | 3/1977 | U.S.S.R. . |
| 1 050 706 | 4/1982 | U.S.S.R. . |
| 1 510 131 | 11/1986 | U.S.S.R. . |
| 1 304 987 | 5/1975 | United Kingdom . |
| 2 045 269 | 10/1980 | United Kingdom . |
| 2 199 839 | 7/1988 | United Kingdom . |
| 90/15083 | 12/1990 | WIPO . |
| 90/15084 | 12/1990 | WIPO . |
| 91/03502 | 3/1991 | WIPO . |
| 93/10176 | 5/1993 | WIPO . |

OTHER PUBLICATIONS

Klee et al, Polymer Bulletin 27 (1992); pp. 511–517.

Chemical Abstract, vol. 89, No. 18, Oct. 30, 1978, Columbis OH, US; Abstract No. 148211C; p. 71, Column 2; abstract & Lakokras Mater. IKH, Primen., No. 4, 1978, pp. 50–52.

Dusek et al; American Chemical Society (1984) Transesterification and Gelation of Polyhydroxy Esters Formed from Diepoxides and Dicarboxylic Acids.

Hartel et al; (Nov. 1984) Zur Synthese linearer Additionspolymere aus Diandiglycidether und Dicarbonsauren.

Klee; Acta Polymer 44, 163–167 (1993); Synthesis and investigation of $\alpha,w$–methacryloyl poly (epoxide–carboxylic acid and $\alpha,w$–methacryloyl poly (epoxide–phenol)–macromonomers.

J. Klee et al, Acta Polymer 42 (1991) 17–20.

Fukushima et al; Dental Materials Journal 4(1): pp. 33–39 (1985): Application of Functional Monomers for Dental Use (Part 9) Sysntheses of Succinoxy Methacrylates and Their Adhesion to Polished and Etched Tooth Surfaces.

Lin et al; Journal of Polymer Science; Part A: Polymer Chemistry, vol. 30, 1941–1951 (1992).

Allard et al; Journal of Polymer Science: Polymer Chemistry Edition, vol. 22, 3827–3842 (1984).

Hage et al; American Chemical Society (1986) Poly(acrylourethane)–Polyepoxide Semi–interpenetrating Networks Formed by Electron–Beam Curing.

Dubuisson et al; Rheol. Acta 20, 463–470 (1981).

Klee; Acta Polymer., 45, 73–82 (1994) Telechelic prepolymers and macromonomers by step growth processes.

John Wiley & Sons; Encyclopedia of Polymer Science and Engineering, vol. 8, Identification to Lignin.

Rot et al, Chemical Abstract, vol. 89, No. 18, Oct. 30, 1978, Columubs, Ohio, US; Abstract No. 148211c; p. 71, column 2, *abstract* & Lakokras Mater. IKH. Primen., No. 4, pp. 50–52, 1978.

Dusek et al, Transesterification & Gelation of Polyhydroy Esters, Formed from Diepoxides & Dicarboxylic Acids, Amer. Chem. Societym 1984.

Hartel et al, Zur Synthese linearer Additionspolymere aus Diandiglycidether und Dicarbonsauren, (Nov. 1984).

Klee et al, Synthesis and investigation of $\alpha,\omega$–methacryloyl poly (epoxide–phenol)–macromonomers, Acta Polymer 44, 163–167 (1993).

Klee et al., Polym Bull. 27 (1992); 511–517.

J. Klee et al., Acta Polym. 42 (1991) 17–20.

Fukushima et al; Dental Materials Journal 4(1): 33–39, 1985; Application of Functional Monomers for Dental Use (Part–9) Syntheses of Succinoxy Methacrylates and Their Adhesion to Polished and Etched Tooth Surfaces.

No. 25211, Apr. 1985, Havant GB, XP002047831.

DENTAL POLYMER PRODUCT

This is a continuation, of application Ser. No. 08/231,535, filed Apr. 22, 1994, now abandoned.

The invention relates to a dental composition or kit of parts for preparing a polymer, to a process for preparing said polymers and polymer products obtained theory, notably artificial teeth.

BACKGROUND OF THE INVENTION

Dental filling materials mainly consist of liquid polymerizable organic monomers and/or polymers, reactive diluents, polymerization initiators, stabilizers, and fillers.

These composite materials have their good mechanical properties such as high flexural strengths, high compressive strengths and their hardness. Furthermore they are polishable and it is possible to adjust their dye. The most frequently used monomers are esters of methyacrylates and higher multifunctional alcoholes or isocyanates such as the bismethacrylate of biphenol-A diglycidyl ether, urethane bismethacrylates.

One of the main disadvantages using composites as dental filling materials is the relatively high shrinkage of organic monomers during polymerization. The shrinkage causes the well known effect of contraction gaps and subsequent cracks. Common dental composites show a shrinkage of 2.5 up to 4.0 vol.-%.

It is well known that the shrinkage directly depends on the molecular weight of polymerizable organic monomers. On the other hand, increasing molecular weights of the monomers are combined with an increasing viscosity of the resin. Therefore reactive diluents such as oligoethyleneglycoidimethacrylates, are necessary to obtain a lower viscosity and the possibility to incorporates the desired amount of fillers. However, reactive diluents show a relatively high shrinkage by themselves, for example 12.89 vol-% for pure triethyleneglycoldimethacrylate.

Moreover, conventional used composites snow a relatively low self-adhesion to teeth, metals are ceramics. In numerous experiments using epoxide polymers and methacryates for the preparation of IPNs (J. Polym. Sci. Part Al Polym. Chem. 30 (1992) 1941, J. Appl. Chrom. 24 (1991) 692, Polym. 31 (1990) 2066,) multiphase systems were obtained which have insufficient mechanical, thermal and optical properties or which result in microphase separated polymers (Acta Polymerica 38 (1987) 547 and DO 226731) with insufficient adhesion to teeth and ceramics.

DESCRIPTION OF THE INVENTION

Therefor it is the object of the invention to provide a process and composition for preparing a polymer composition for dental purposes exhibiting a low shrinkage and a high self-adhesion to ceramics and metals.

This object is advanced by a process according to claim 1. Preferably the macromonomers have a generally formula I or II:

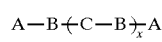

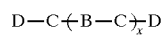

wherein A and D are unsaturated moieties, B is a moiety arisen from a diepoxide or a diisocyanate and C is a HX-residue selected from the group consisting of —OH, —COCH, —NH$_2$, —NH—, —SH.

The macromonomers I and II preferably are α,ω-terminated poly (epoxide-carboxylic acid) macromonomers of formulas M-1, M8 and M-9, α,ω-terminated poly (epoxide-amine) macromonomers of formulas M-2 to M-5, M-10 and M-1 I or α,ω-terminated poly(epoxide-phenol) macromonomers of formulas M-6, M-7 and M-12 are described in the following literature (J. Klee, H.-H. Hörhold, H. Schötz, Acta Polym. 42 (1991) 17–20; J. Klee et. al. Polym. Bull. 27 (1992) 511–517) and in the patent literature (DD 277 689, DD 279 667, DE-P 42 17 761.8). They are characterized by the structures M-1 to M-12:

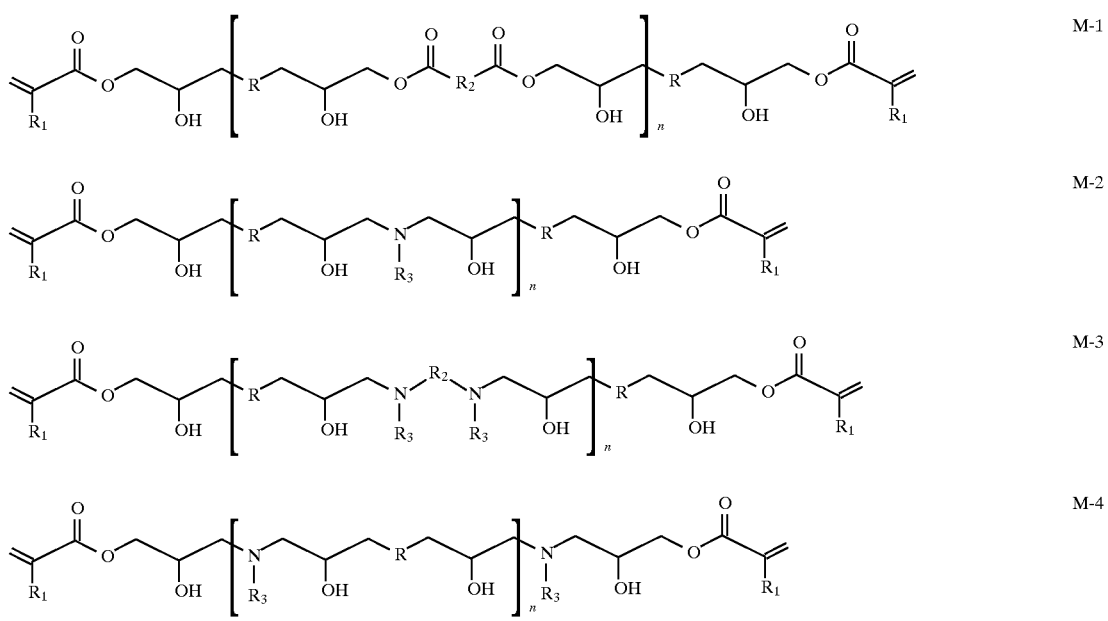

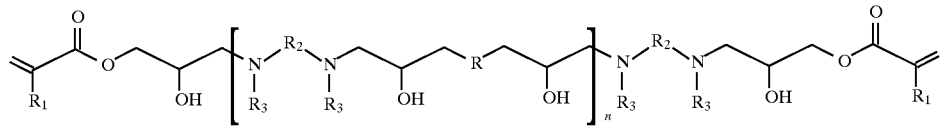 M-5
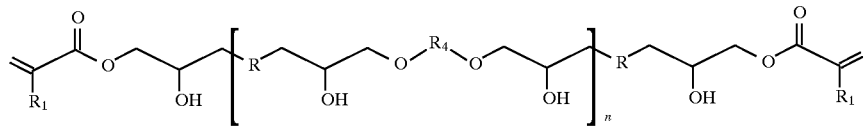 M-6
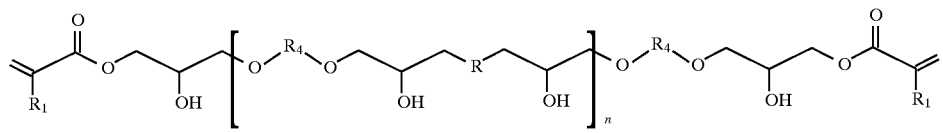 M-7
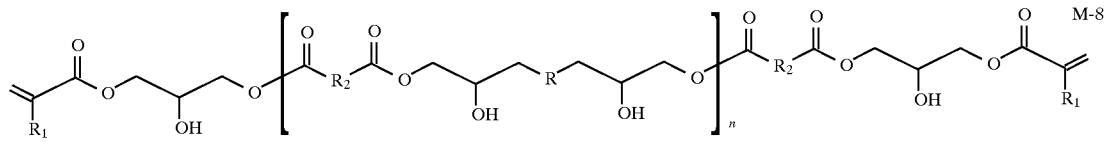 M-8
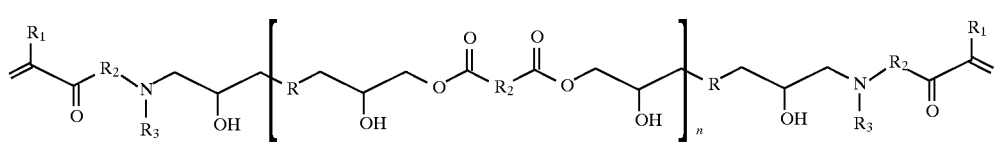 M-9
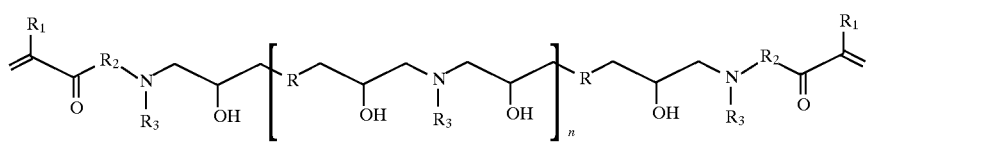 M-10
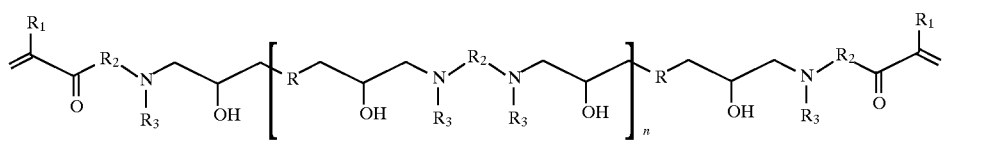 M-11
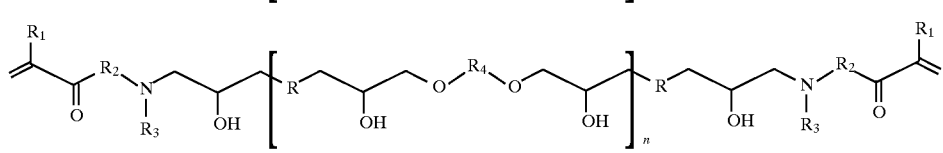 M-12
wherein
R is a residue derived from a diepoxide, notably a residue of the following formula
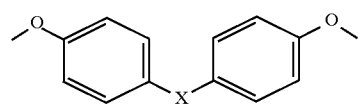
whereby X is $C(CH_3)_2$, $-CH_2-$, $-O-$, $-S-$, $-CO-$, $-SO_2-$
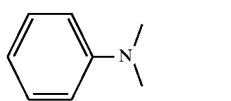
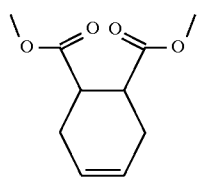

$R_1$ denotes hydrogen or a substituted or unsubstituted $C_1$ to $C_{12}$ alkyl group or an oxyalkyl group, $C_2$ to $C_{12}$ alkenyl group, $C_5$ to $C_{12}$ cycloalkyl, $C_6$ to $C_{12}$ aryl or $C_7$ to $C_{12}$ aralkyl $R_2$ is a difunctional substituted or unsubstituted $C_1$ to $C_{12}$ alkyl group, $C_2$ to $C_{12}$ alkenyl group, $C_5$ to $C_{12}$ cycloalkyl, $C_6$ to $C_{12}$ aryl or $C_7$ to $C_{12}$ aralkyl, $R_3$ denotes hydrogen or a substituted or unsubstituted $C_1$ to $C_{12}$ alkyl group, $C_2$ to $C_{12}$ alkenyl group, $C_5$ to $C_{12}$ cycloalkyl, $C_6$ to $C_{12}$ aryl or $C_7$ to $C_{12}$ aralkyl, $R_4$ is a substituted or unsubstituted $C_6$ to $C_{12}$ aryl, such as

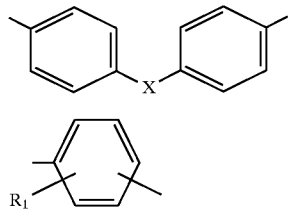

whereby X is $C(CH_3)_2$, $-CH_2-$, $-O-$, $-S-$, $-CO-$, $-SO_2-$ and n is an integers of n=1, 2, 3, 4, 5, 6, 7, 8

Macromonomers M-1, M-2, M-3, M- are synthesised in two steps. At first by reaction of excessive bisphenol-A diglycidyl ether DGEBA, bisphenol-F diglycidyl ether DGEBF, butanediol diglycidyl ether BDODGE, tetrahydro terephtalic acid diglycidyl ether or diglycidyl aniline and methacryoic acid MAA (x>2y) an oligomer mixture is obtained. This mixture contains the bismethacrylate of DGEBA (Bis-GMA, n=0) along with mono-GMA and unreacted DGEBA as well as governed by the epoxide-comonomer ratio. The formation of macromonomers follows in a second reaction of DGEBA and mono-GMA, respectively with primary monoamines to M-2, disecondary diamines to M-3 (J. Klee et al. Polym.Bull. 27 (1992) 511–517, DD 279667), carboxylic acids to M-1 (DE 4217761.8), or biphenols to M-6 (J. E. Klee et al., Acta Polym. 44 (1993) 163).

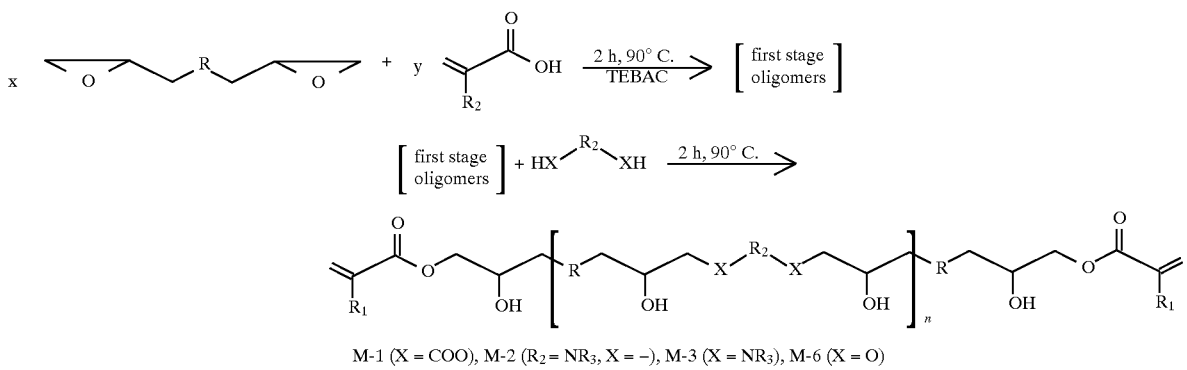

M-1 (X = COO), M-2 ($R_2$ = $NR_3$, X = -), M-3 (X = $NR_3$), M-6 (X = O)

During the epoxide ring cleavage by carboxylic acids an amount of approximately 20% of the epoxide groups is opened to the corresponding primary alcohols. Consequently, macromonomers M-1, M-2, M-3 and M-6 contains booth types of molecules having primary and/or secondary alcohol units.

Macromonomers M-4 and M-5 are prepared by one- or two-step reactions of the diepoxides, primary monoamines or disecondary diamines and 2,3-epoxypropyl-metharylate using amine in excess and a mol ratio a<b, and 2c+a=b. The macromonomers M-4 and M-5 also obtainable by terminating reaction of α,ω-amino terminated prepolymers with 2,3-epoxypropyl-methacrylate (DD 277689, J.Klee, H.-H. Hörhold, H. Schütz, Acta Polym. 42 (1991) 17–20).

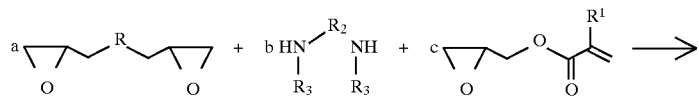

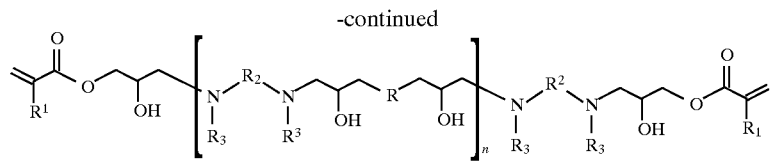

M-5, M-4 (R₃NH₂)

Instant of amines also were used bisphenols or dicarboxylic acids to produce macromonomers M-7 and M-8, respectively.

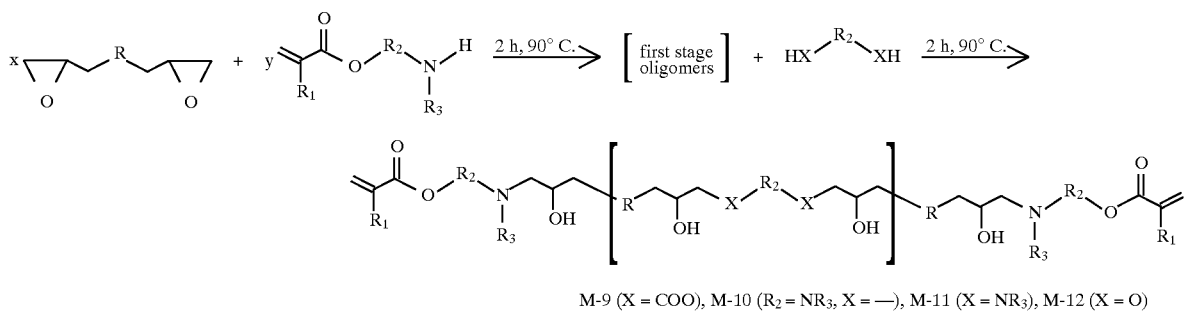

M-9 (X = COO), M-10 (R₂ = NR₃, X = —), M-11 (X = NR₃), M-12 (X = O)

Macromonomers M-9 to M-12 are prepared by one- or two-step reactions of the diepoxides, primary monoamines, disecondary diamines, dicarboxylic acids, or phenols and amino alkyl methacrylates.

The polymer composition comprises α,ω-terminated poly(urethane) macromonomers, α,ω-terminated poly(urea) macromonomers or α,ω-terminated poly(thiourethane) macromonomers of the following formulas M-1 3 to M-24 which are polymerizable in a mixture with di-or polyepoxides and/or di- or polyisocyanates and polyamines and/or primary monoamines and/or disecondary diamines or dicarb-oxylic acids, dicarboxylic acid anhydrides, diphenols, or dithioles:

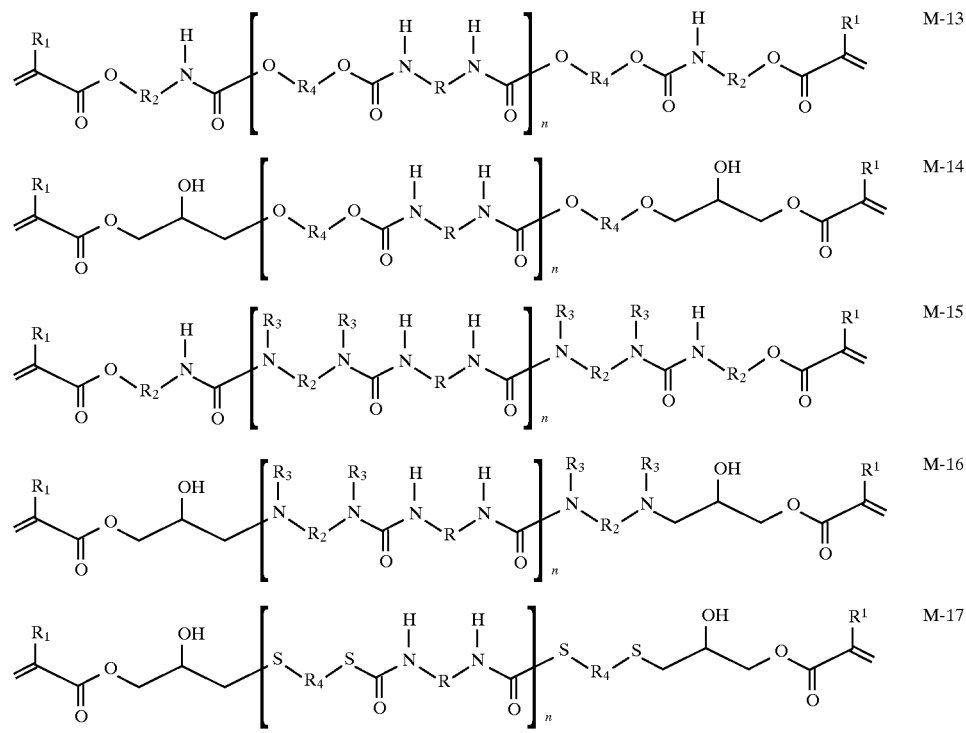

-continued

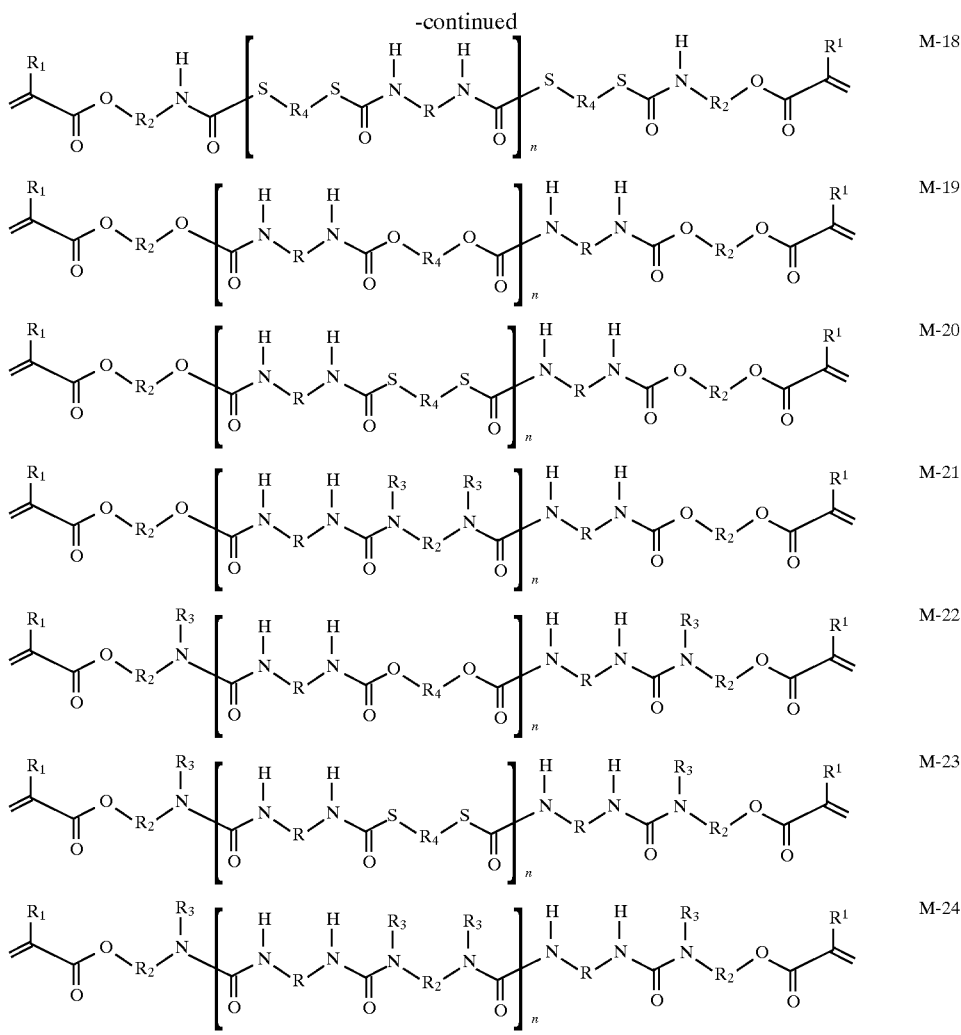

wherein

R is a residue derived from a diisocyanate, notably a residue of the following formula

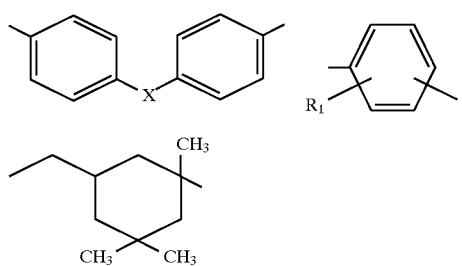

$R_1$ denotes hydrogen or a substituted or unsubstituted $C_1$ to $C_{12}$ alkyl group, $C_2$ to $C_{12}$ alkenyl group, $C_5$ to $C_{12}$ cycloalkyl, $C_6$ to $C_{12}$ aryl or $C_7$ to $C_{12}$ aralkyl $R_2$ is a difunctional substituted or unsubstituted $C_1$ to $C_{12}$ alkyl group, $C_2$ to $C_{12}$ alkenyl group, $C_5$ to $C_{12}$ cycloalkyl, $C_6$ to $C_{12}$ aryl or $C_7$ to $C_{12}$ aralkyl $R_3$ denotes hydrogen or a substituted or unsubstituted $C_1$ to $C_{12}$ alkyl group, $C_2$ to $C_{12}$ alkenyl group, $C_5$ to $C_{12}$ cycloalkyl, $C_6$ to $C_{12}$ aryl or $C_7$ to $C_{12}$ aralkyl, $R_4$ is a substituted or unsubstituted $C_6$ to $C_{12}$ aryl, such as

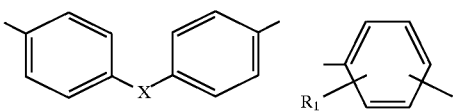

whereby X is $C(CH_3)_2$, $-CH_2-$, $-O-$, $-S-$, $-CO-$, $-SO_2-$ and n is an integers of n=1, 2, 3, 4, 5, 6, 7, 8, . . .

It is possible to use the polymer composition as an one-part composition or as two part-composition. A two-part composition which is mixed immediately before use contains for example the following substances in the parts A and B:

part A: macromonomer, reactive diluent, di- or polyepoxide or di-or polyisocyanate and polymerization initiator part B: macromonomer, reactive diluent, coinitiator and amine or dicarboxylic acid, dicarboxylic acid anhydride, diphenol, or dithiol, respectively.

The composition contains 1 to 99 mol-% of a macromonomer relative to to said monomers, preferably 10 to 90 mol-% of a macromonomer relative to to said monomers, most preferably 30 to 70 mol-% of a macromonomer relative to to said monomers.

The prepared adhesives, adhesive cements and composites are polymerizable in two different polymerization reactions, namely in a free-radical/photochemical and a thermal polymerization reaction which may run subsequently or simultaneously. In both cases interpenetrating networks or semi-IPNs were prepared depending on the comonomer used for the addition reaction namely if polyamines, primary monoamines, disecondary diamines or dicarboxylic acids, dicarboxylic acid anhydrides, diphenols or dithiols were used for epoxide-addition polymerization. The methacrylate networks and the epoxide networks and linear polymers, respectively are compatible. The invented polymer compositions exhibit advantageous mechanical properties and a small shrinkage during polymerization.

The invented polymer compositions may contain reactive diluents such as diethyleneglycoldimethacrylate, triethyleneglycoldimethacrylate, polypropyleneglycoldimethacrylate, methacrylate substituted spiroortho esters, glycerintrimethacrylate, furfurylmethacrylate, urethandimethacrylate, Bis-GMA in a content of 5 to 50 wt-%.

The invented polymer compositions may contain stabilisers such as hydroquinon or 2,6-di-tert.-butyl-p-cresol.

The invented polymer compositions may comprise redox-initiator systems such as azobisisobutyronitril, dibenzoyiperoxid/amine, Cu-acetylacetonate/Li-sulfinate, trialkylboranes or photo initiators such as benzoinmethylether, benzilketal, camphor quinon or acylphosphinoxides in contents of 0,1 to 3 wt-%.

When using the invented polymer compositions as composite, fillers can be mixed into the epoxidelmacromonomer or isocyanate/macromonomer matrix. As fillers were used inorganic glasses such as barium-alumosilicat glasses, silica gels, xero gels or inorganic compounds such as $La_2O_3$, $ZrO_2$, $BiPO_4$, $CaWO_4$, $BaWO_4$, $SrF_2$, $Bi_2O_3$ or organic fillers such as broken organic polymers.

The invented polymer compositions reveals interesting mechanical properties such as a high flexural and compressive strength, a low expansion, good adhesion to metal, glass and ceramics, a low shrinkage and a high radio-opacity between RO=2 and 10 mm/mm Al depending on the nature of the filler used.

When applying the invented dual curing material as adhesive, the viscosity and the adhesion properties of the material are adjustable through evaluation of the macromonomer and the chain length of these In many cases reactive diluents are necessary for the use of the invented materials

REFERENCE EXAMPLE 1

Preparation of macromonomer M-2 (n=1, R=—$OC_6H_4$—$C(CH_3)_2$—$C_6H_4O$—, $R_1$=$CH_3$—, $R_3$=$C_6H_4COOC_4H_9$)

20,000 g (58,75 mmol) bisphenol-A diglycidyl ether, 5,058 g (58,75 mmol) methacrylic acid, 0,253 g triethylbenzylammoniumchlorid, 0,194 g 2,6-di-tert.-butyl-p-cresol (BHT), 7,747 g triethyleneglycoldimethacrylate and 5,677 g (29,38 mmol) p-amino-benzoic butyl ester were mixed and reacted for 16 hours at 80° C. In the IR-spectrum of the macromonomer no absorption of epoxide groups at 915 $cm^{-1}$ was found.

REFERENCE EXAMPLE 2

Preparation of macromonomer M-3 (n=1, R=—$OC_6H_4$—$C(CH_3)_2$—$C_6H_4O$—, $R_1$=$CH_3$—, $R_2$=—$(CH_2)_4O(CH_2)_4$—, $R_3$=$C_6H_5CH_2$—)

150,000 g (0,441 mol) bisphenol-A diglycidyl ether, 37,935 g (0,441 mol) methacrylic acid, 27000 g triethylbenzylammonium chloride, 1,115 g 2,6-di-tert.-butyl-pcresol (BHT) and 111,695 g ethoxylated Bis-GMA were homogeneously mixed under slow heating. The mixture was kept for two hours at 90° C. After this time 75,020 g (0,221 mol) N,N'-dibenzyl-5-oxanonanediamine-1,9 were added to the mixture while stirring and was kept for additional two hours at 90° C. The obtained methacrylate terminated macromonomer is soluble in organic solvents such as chloroform, DMF and THF. In the IR-spectrum no absorption of epoxide groups at 915 and 3050 $cm^{-1}$ was observed. A new absorption of ester groups was found at 1720 $cm^{-1}$.

REFERENCE EXAMPLE 3

Preparation of macromonomer M-5 (n=1, R=—$OC_6H_4$—$C(CH_3)_2$—$C_6H_4O$—, $R_1$=$CH_3$—, $R_2$=—$(CH_2)_4O(CH_2)_4$—, $R_3$=$C_6H_5CH_2$—)

20,000 g (58,75 mmol) bisphenol-A diglycidyl ether and 40,012 g (117,50 mmol) N,N'-dibenzyl-5-oxanonanediamine-1,9 were homogeneously mixed under slow heating. The mixture was kept for two hours at 90° C. After this time 16,704 g (117,50 mmol) 2,3-epoxypropyl methacrylate were added to the mixture while stirring and were kept for another two hours at 90° C. The obtained methacrylate terminated macromonomer is soluble in organic solvents such as chloroform, DMF and THF. In the IR-spectrum no absorption of epoxide groups at 915 and 3050 $cm^{-1}$ were observed.

REFERENCE EXAMPLE 4

Preparation of macromonomer M-21 (n=1, $R_1$=$CH_3$—, $R_2$=—$CH_2CH_2$—, $R_4$=—$(CH_2)_2O(CH_2)_2O(CH_2)_2$—,)

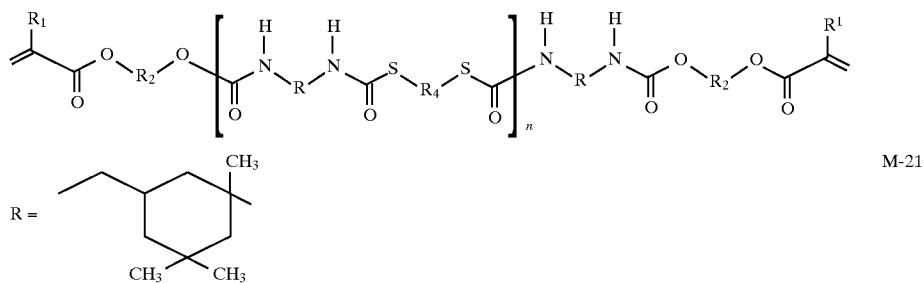

M-21

15,000 g (67,790 mmol) isophorondiisocyanate, 6,179 g (33,895 mmol) 1,8-dimercapto-3,6-dioxaoctane, 8,822 g (67,790 mmol) hydroxyethylmethacrylate and 0,060 g BHT were homogeneously mixed and reacted for 8 h hours at 45° C. The obtained macromonomer does not show an absorption of the isocyanate group at 2200 $cm^{-1}$ in the IR spectrum.

EXAMPLE 1–5

3,0 g (15,4 mmol) 3(4),8(9)-Bis(aminomethyl)tricyclo-5.2.1.0.$^{2,6}$-decan TCD and 10,5 g (30,8 mmol) 2,2-Bis[4(2,3-epoxypropoxy)phenyl]propane DGEBA were mixed to give the epoxide-amine addition polymer AP. Different amounts (see table 1) of macromonomer M-5 (n=0, R=—OC$_6$H$_4$—C(CH$_3$)$_2$—C$_6$H$_4$O—, R$_1$=CH$_3$—, R$_2$=—(CH$_2$)$_4$O(CH$_2$)$_4$—, R$_3$=C$_6$H$_5$CH$_2$) N,N'-Dibenzyl-N,N'-bis-(2-hydroxy-3-methacryloyloxypropyl)-5-oxanonandiamin-1,9, and 0.5% photo initiator IRGACURE 651 (Ciba Geigy) were added and the parts thoroughly mixed. To remove gas bubbles the mixture was exposed to vacuum of an oil pump and then filled into moulds to prepare test samples for dynamic mechanic analysis (DMA). Methacrylate groups were polymerized upon exposure to UV light of a stroboscope UV lamp for 6 minutes. Then the samples were already stiff enough to be released from the mould. The polymerization of epoxide with amine was then completed by storing over night at 85° C.

The glass transition temperatures of the resulting materials were determined by differential scanning calorimetry (DSC) and the maximum of tan δ in DMA. Results are shown in table 1. Only one glass transition appears. Under scanning electron microscope phase separation is not being found (resolution 500 nm).

TABLE 1

Composition and glass temperatures of IPN and homopolymers of M-5 and AP

| | originally weight-in quantity of | | | | | | ratio of | Tg | Tg |
|---|---|---|---|---|---|---|---|---|---|
| | DGEBA | | TCD | | M-5 | | M-5/AP | (DSC) | (DMA) |
| Example | g | mmol | g | mmol | g | mmol | wt-% | °C. | °C. |
| M-5 | — | — | — | — | 10,0 | 16,0 | 100/0 | 10 | 18 |
| 1 | 2,00 | 5,88 | 0,57 | 2,94 | 25,70 | 41,13 | 90/10 | 9 | 20 |
| 2 | 5,00 | 14,69 | 1,43 | 7,71 | 19,29 | 30,87 | 75/25 | 37 | 36 |
| 3 | 10,50 | 30,84 | 3,00 | 15,42 | 13,50 | 21,61 | 50/50 | 60 | 69 |
| 4 | 10,50 | 30,84 | 3,00 | 15,42 | 4,50 | 7,20 | 25/75 | 98 | 103 |
| 5 | 10,50 | 30,84 | 3,00 | 15,42 | 1,94 | 3,11 | 10/90 | 140 | 125 |
| AP | 10,50 | 30,84 | 3,00 | 15,42 | — | — | 0/100 | 154 | 156 |

EXAMPLE 6 (one-paste system)

3,000 g of macromonomer M-2 of reference example 1 and 1,142 g (3,35 mmol) bisphenol-A diglycidyl ether, 1,142 g (3,35 mmol) N,N'-Dibenzyl-5-oxanonandiamine-1.9 and 0.02 g camphor quinon were homogeneously mixed and polymerized as described in example 1–5. The shrinkage of the photochemical polymerization is 0,68 vol-% and of the thermal addition polymerization 2,44 vol-%.

EXAMPLE 7 (one-paste system)

3,000 g of macromonomer M-2 of reference example 1 were homogeneously mixed with 1,142 g (3,35 mmol) bisphenol-A diglycidyl ether, 0,806 g (3,35 mmol) N,N'-dibenzylethylenediamine and 0,02 g camphor quinon and polymerized as described in example 1–5. The shrinkage of the photochemical polymerization is 0,56 vol-% and of the thermal addition polymerization 3,43 vol-%.

EXAMPLE 8 (one-paste system)

3,000 g of macromonomer M-2 of reference example 1 were homogeneously mixed with 1,142 g (3,35 mmol) bisphenol-A diglycidyl ether, 0,176 g (1,34 mmol) N,N-dipropylenetriamine and 0,02 g camphor quinon and polymerized as described in example 1–5. A shrinkage of dV=3,5%, dV=1,8% was measured which is caused by the photochemical step and dV=1,7% which is caused by the thermal epoxide-amine addition polymerization.

EXAMPLE 9 (two-paste system)

Part A)

2,000 g of macromonomer M-2 of reference example 1 were homogeneously mixed with 4,246 g (3,35 mmol) Araldit-F, 0,054 g dibenzoylperoxide 19,500 g of a mixture of CaWO$_4$/ZrO$_2$ (4:1) and 0,100 g aerosil.

Part B)

2,000 g of macromonomer M-2 of reference example 1 were homogeneously mixed with 1,086 g (5,59 mmol) 3(4),8(9)-bis(amino methyl)-tricyclo-5.2.1.0.$^{2,6}$-decan, 0,054 g N,N-bis(β-hydroxyethyl)-p-aminobenzoic acid ethylester, 9,441 g of a mixture of CaWO$_4$/ZrO$_2$ (4:1) and 0,100 g aerosil.

Parts A and B were mixed immediately before use in a weight ratio of 2:1 and polymerized for 10 minutes at 37° C. The shrinkage was measured as follows: dV=0,99 vol.-% and the radio-opacity RO=8,3 mm/mm Al.

EXAMPLE 10 (two-paste system)

Part A)

10,000 g of macromonomer M-3 of reference example 2 were homogeneously mixed with 7,010 g (20,60 mmol) Araldit MY-790, 0,010 g dibenzoylperoxide and 23,000 g Barium-Alumosilicate-glass and 0,100 g aerosil.

Part B)

2,000 g of macromonomer M-3 of reference example 2 were homogeneously mixed with 2,001 g (10,30 mmol) 3(4),8(9)-bis(amino methyl)-tricyclo-5.2.1.0.$^{2,6}$-decan, 0,015 g N,N-bis(β-hydroxyethyl)-p-aminobenzoic acid ethyl ester, 22,000 g Barium-Alumo-silicate-glass and 0,100 g aerosil.

Parts A and B were mixed immediately before use in a weight ratio of 1:0,706 and polymerized at 37° C. for 10 minutes. The shrinkage was measured of dV=1,55 vol.-%.

EXAMPLE 11 (two-paste system)

Part A)

10,000 g of macromonomer M-5 of reference example 3 were homogeneously mixed with 7,010 g (20,60 mmol) Araldit MY-790 and 0,010 g dibenzoylperoxide.

Part B)

10,000 g of macromonomer M-5 of reference example 3 were homogeneously mixed with 2,001 g (10,30 mmol)

3(4),8(9)-bis(amino methyl)-tricyclo-5.2.1.0.$^{2,6}$-decan and 0,015 g N,N-bis(β-hydroxy-ethyl)-p-aminobenzoic acid ethyl ester.

Parts A and B were mixed immediately before use in a weight ratio of 1:0,707. The first polymerization step occurs during radiation at λ>365 nm for 360 seconds and the second step as thermal epoxide-amine polymerization at 85° C. for 16 hours. The following values were measured: Tg=69° C., ΔV=1,75 vol.-%.

EXAMPLE 12 (one-paste system)

8,650 g (7,25 mmol) of macromonomer M-5 of reference example 3 (R=—OC$_6$H$_4$—C(CH$_3$)$_2$—C$_6$H$_4$O—, R$_1$=CH$_3$—, R$_2$=—(CH$_2$)$_4$O (CH$_2$)$_4$—, R$_3$=C$_6$H$_5$CH$_2$—), 3,707 g triethyleneglycoldimethacrylate, 1,35 g (3,62 mmol) 3(4),8(9)-Bis(aminomethyl)tricyclo-5.2.1.0.$^{2,6}$-decan, 2,467 g (7,25 mmol) bisphenol-A diglycidyl ether, 0,124 g camphor quinon and 0,124 g N,N-bis(,-hydroxy-ethyl)-p-toluidine were mixed homogenously immeadely befor use. A smal layer of this mixture was put on a ceramic tooth and polymerized with visible light for 40 seconds. Thereafter a composite TP.H (De Trey Dentsply) was applied to this layer and polymerized for 40 seconds. Then material was reacted for 24 hours at 37° C. After this time the adhesion of the material is 7,4±1,3 MPa.

Comparison example (Acta Polym. 38 (1987) 547)

7,000 g (13,66 mmol) Bis-GMA, 3,000 g triethyleneglycoldimethacrylate, 5,0960 g (14,97 mmol) bisphenol-A diglycidyl ether, 4,917 g (14,97 mmol) N,N'-Dibenzyl-3,6-dioxactanediamine-1,8 (Acta Polym. 38 (1987) 547 and DD 226731), 0,050 g camphor quinon and 0,0050 g N,N-bis(β-hydroxy-ethyl)-p-toluidine were mixed homogenously immeadely befor use. A smal layer of this mixture was put on a ceramic tooth and polymerized with visible light for 40 seconds. Thereafter a composite TP. H (De Trey Dentsply) was applied to this layer and polymerized for 40 seconds. Then the material was reacted in water for 24 hours at 37° C. After this time the adhesion of the material is 4,1±1,2 MPa.

EXAMPLE 13 (two-paste system)

5,000 g (7,532 mmol) of M-21, 1,373 g (7,532 mmol) 1,8-dimercapto-3,6-dioxaoctane, 2,564 g (7,532 mmol) bisphenol-A diglycidyl ether, 0,089 g camphor quinon and 0,089 g N,N-bis(β-hydroxy-ethyl)-p-toluidine were mixed homogenously immeadely befor use. A smal layer of this mixture was put on a ceramic tooth and polymerized with visible light for 40 seconds. Thereafter a composite TP.H (De Trey Dentsply) was applied to this layer and polymerized for 40 seconds. Then the material was reacted in water for 24 hours at 37° C. After this time the adhesion of the material is 6,9±0,7 MPa.

What we claim is:

1. A dental filling process comprising the steps of
A. preparing a liquid mixture comprising
   (i) at least one macromonomer selected from the group consisting of epoxide-amine macromonomer, epoxide-phenol macromonomer and epoxide-carboxylic acid macromonomer, said macromonomer having at least two double bonds,
   (ii) at least one polyaddition component having at least two moieties capable of addition reaction selected from the group consisting of epoxide and isocyanate moieties and
   (iii) an H-active component having at least two HX-residues selected from the group consisting of

—NH$_2$,—HN—, —SH

B. polymerizing said macromonomer (i)
C. subjecting said polyaddition component (ii) and said H-active component (iii) to a polyaddition reaction at about 37° C. whereby steps B and C are carried out in a layer on a tooth either simultaneously or one after the other characterized in that a single-phase polymer composition having an interpenetrating network with a single glass transition temperature is prepared from 1 to 99 mole percent of said macromonomer (i) polymerized in step B whereby said macromonomer has a molecular weight of at least 600 and contains at least one structural unit which is of the same type as a repetitive unit produced by polyaddition of (ii) and (iii) in presence of 0.1 to 5 percent by weight of a polymerization initiator and applying polymerizable composite material to said layer and polymerizing said composite material whereby said composite material adheres to said tooth with an adhesion of at least about 6.9 MPa.

2. The process for preparing a polymer composition of claim 1 wherein the said macromonomer is within the scope of one of the following formulas I and II

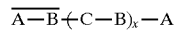  I

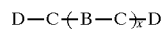  II wherein A and D are unsaturated moieties, B is a moiety derived from a diepoxide or a diisocyanate and C is at least a moiety having two H-active residues selected from the group consisting of —OH, —COOH, —NH$_2$, —NH—, —SH—.

3. The process for preparing a polymer composition as claimed in claim 2 wherein said macromonomers and addition polymers are in a weight ratio between 30:70 and 70:30.

4. The process for preparing a polymer composition of claim 1 wherein each said macromonomer is δ,ω-terminated poly(epoxide-carboxylic acid) macromonomer within the scope of formulas M-1, M-8 and M-9, δ,ω-terminated poly(epoxide-amine) macromonomer within the scope of one of formulas M-2, M-3. M-4, M-5, M-10 and M-11 or δ,ω-terminated poly(epoxide-phenol) macromonomer within the scope of one of formulas M-6, M-7 and M-12

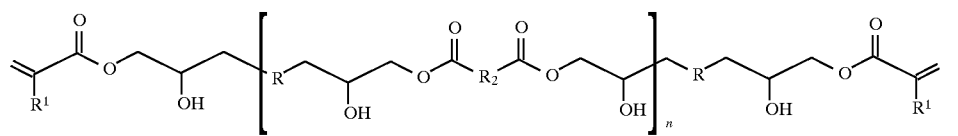
M-1
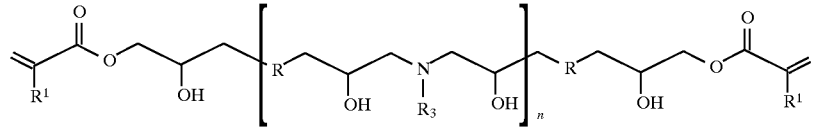
M-2
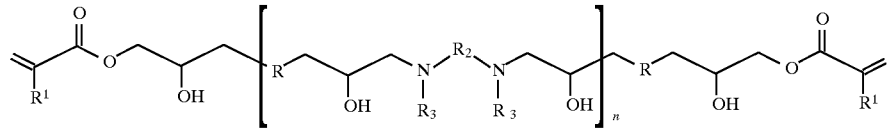
M-3
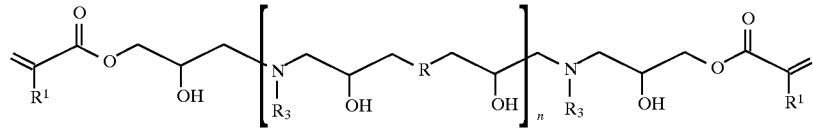
M-4
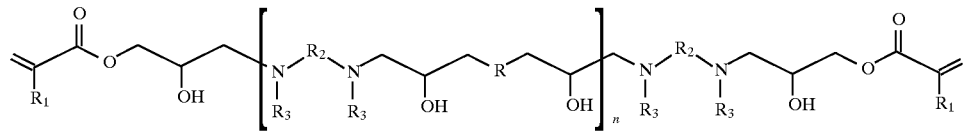
M-5
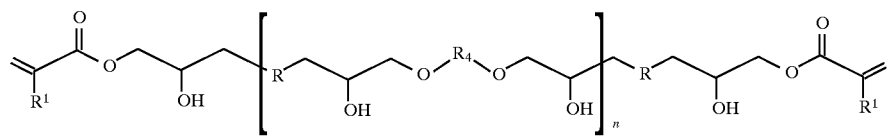
M-6
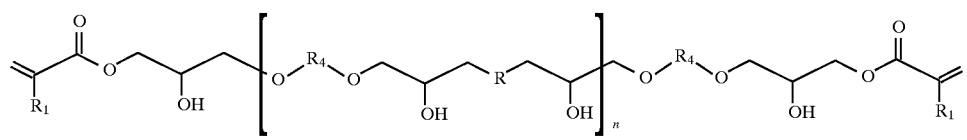
M-7
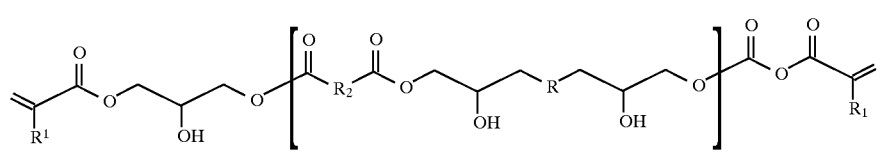
M-8
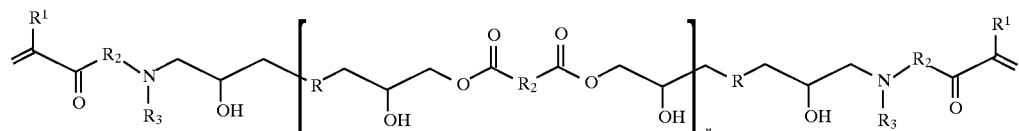
M-9
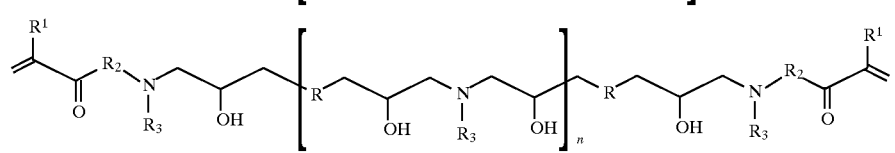
M-10
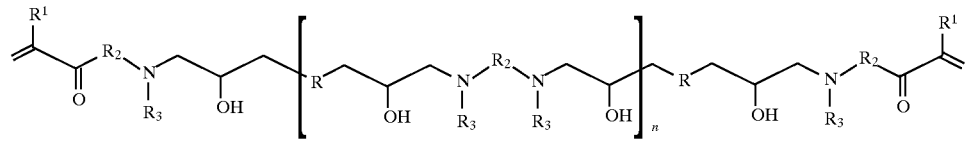
M-11
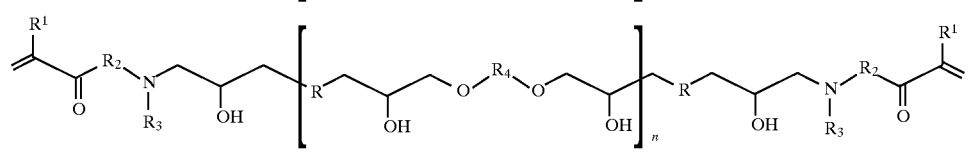
M-12 wherein
R is a residue derived from a diepoxide, notable a residue of the following formula

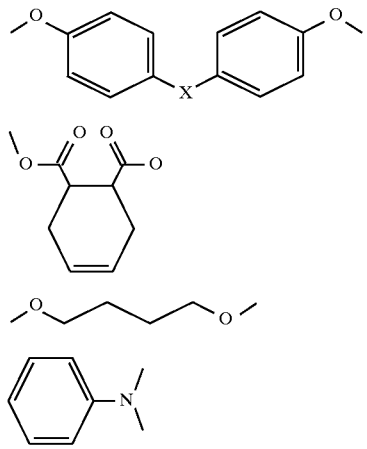

whereby X is C(CH$_3$)$_2$, —CH$_2$—, —O—, —S—, —CO—, —SO$_2$—

R$_1$ denotes hydrogen or a substituted or unsubstituted C$_1$ to C$_{12}$ alkyl group or an oxyalkyl group, C$_2$ to C$_{12}$ alkenyl group, C$_5$ to C$_{12}$ cycloalkyl, C$_6$ to C$_{12}$ aryl or C$_7$ to C$_{12}$ aralkyl R$_2$ is a difunctional substituted or unsubstituted C$_1$ to C$_{12}$ alkyl group, C$_2$ to C$_{12}$ alkenyl group, C$_5$ to C$_{12}$ cycloalkyl, C$_6$ to C$_{12}$ aryl or C$_7$ to C$_{12}$ aralkyl R$_3$ denotes hydrogen or a substituted or unsubstituted C$_1$ to C$_{12}$ alkyl group, C$_2$ to C$_{12}$ alkenyl group, C$_5$ to C$_{12}$ cycloalkyl, C$_6$ to C$_{12}$ aryl or C$_7$ to C$_{12}$ aralkyl R$_4$ is a substituted or unsubstituted C$_6$ to C$_{12}$ aryl, such as

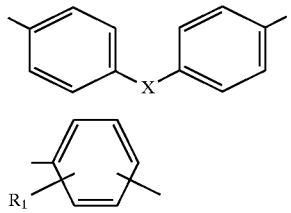

whereby X is C(CH$_3$)$_2$, —CH$_2$, —O—, —S—, —CO—, —SO$_2$— and n is an integer from =1 to 8.

5. The process for preparing a polymer composition of claim 1 wherein said macromonomer and addition polymers are in a weight ratio between 30:70% and 70:30%.

6. The process for preparing a polymer composition of claim 1 wherein said liquid mixture further comprises reactive diluent selected from the group consisting of triethyleneglycol bismethoacrylate, diethyleneglycol bismethacrylate, dioxolan bismethacrylate, vinyl-, vinyleneor vintylidenacrylate- or methacrylate substituted spiroorthoesters, spiroorthocarbonates or bicyloortho esters, and ethoxylated (2,2-Bis-[p-(2-hydroxy-3-methacryloyloxypropoxy)-phenyl]-propane) (Bis-GMA), in a content of 5 to 50 percent by weight.

7. The process for preparing a polymer composition of claim 1 wherein said liquid mixture further comprises di- or polyepoxide selected from a group consisting of bisphenol-A diglycidyl ether, bisphenol-F diglycidyl ether, novolakepoxides, N,N,N',N'-tetraglycidyl diaminodiphenylmethan and Δ$^3$-tetrahydrophthalic acid diglycidyl ester.

8. The process for preparing a polymer composition of claim 1 wherein said liquid mixture further comprises primary monoamine benzyleamine, 1-adamantanamine, α-phenethylamine and ethanol amine and selected from a group consisting of disecondary diamines N,N'-dibenzylethylenediamine, N,N'-dimethyl-ethylenediamine, and N,N'-dibenzyl-3,6-dioxaoctandiamine-1,8N,N'-dibenzyl-5-oxanonandiamine-1,9; N,N'-dibenzyl-(2,2,4)(2,4,4)-trimethylhexamethylenediamine and polyamines selected from the group consisting of N,N-dipropylenetriamine, tripropylenetetramine, isophorondiamine, (2,2,4)(2,4,4)-trimethylhexamethylenediamine-1,6; 3(4),8(9)-bis(amino methyl) tricyclo-5.2.1.0$^{2.6}$-decan and O,O'-bis-amino (polypropyleneglycol).

9. The process for preparing a polymer composition of claim 1 wherein said liquid mixture further comprises photo initiator selected from the group consisting of benzoinmethylether, benzilketal, camphorquinon, acylphosphinoxides in a ratio of 0.1 to 3 percent by weight.

10. The process for preparing a polymer composition of claim 1 wherein said liquid mixture further comprises thermal initiators selected from the group consisting of azobisisbutyronitril and dibenzoylperoxid in a portion of 0.1 to 3 percent by weight or redox initiator systems.

11. The process for preparing a polymer composition of claim 1 polymerizing photochemically for 10 to 300 seconds having a rapid fixation followed by the thermal polymerization in a temperature range of 20° to 200° C. during 0.5 to 40 hours.

12. The process for preparing a polymer composition of claim 1 polymerizing in two thermal initiated steps whereas the first polymerization occurs at 35° to 130° C. for 10 to 600 seconds and the second polymerization occurs at 20° to 200° C. for 0.5 to 40 hours.

13. The process for preparing a polymer composition of claim 1 wherein said liquid mixture further comprises filler particles selected from the group consisting of barium-alumosilicate glass, xerogel La$_2$O$_3$, ZrO$_2$, BiPO$_4$, CaWO$_4$, SrF$_2$, Bi$_2$O$_3$ organic polymer.

14. The process for preparing a polymer composition of claim 1 containing dye pigments.

15. The process for preparing a polymer composition of claim 1 prepared as a two-part system comprising two pastes, which require mixing prior to their application wherein a first paste comprising at least one said macromonomer, a polyepoxide, a filler, a polymerization initiator and a second paste comprising at least one said macromonomer, an amine, a diphenol or a dicarboxylic acid, a filler and a part of the polymerization initiator or coinitiator.

16. The process for preparing a polymer composition of claim 1 wherein said interpenetrating network comprises at least one network polymer and at least one linear addition polymer which is obtained by polyaddition of a diepoxide and a primary monoamine or a disecondary diamine.

17. A kit of parts for performing the process of claim 1 comprising (i) at least one epoxide-amine macromonomer, one epoxide-phenol macromonomer or one epoxide-carboxylic acid macromonomer having at least two double bonds and a second component of (ii) at least one polyaddition component having at least two moieties capable of addition reaction selected from the groups consisting of epoxide or isocyanate moieties and (iii) at least one H-action component having at least two HX-residues selected from the group consisting of —OH, —COOH, —NH$_2$, —NH—, —SH.

18. Polymer composition obtained by the process according to claim 1.

19. An artificial dental tooth composed of said polymer of claim 18.

20. The process for preparing a polymer composition of claim 1 wherein said macromonomer and addition polymer are in a weight ratio between 30:70 and 70:30.

* * * * *

UNITED STATES PATENT AND TRADEMARK OFFICE
CERTIFICATE OF CORRECTION

PATENT NO. : 5,876,210
DATED : March 2, 1999
INVENTOR(S) : Klee, et. al.

It is certified that error appears in the above-indentified patent and that said Letters Patent is hereby corrected as shown below:

In column 1, line 7 of the Patent, change "theory" to ---thereby--.

In column 1, line 40 of the Patent, change "snow" to --show--.

In column 1, line 41 of the Patent, change "are " to --and--.

In column 2, line 29 of the Patent, change "COCH" to --COOH--.

Signed and Sealed this

Thirtieth Day of November, 1999

Attest:

Q. TODD DICKINSON

*Attesting Officer*   *Acting Commissioner of Patents and Trademarks*